(12) United States Patent
Chalkidis et al.

(10) Patent No.: US 11,526,810 B2
(45) Date of Patent: Dec. 13, 2022

(54) SYSTEM FOR PREDICTION MODEL MANAGEMENT WITH TREATMENT PATHWAYS AND BIOMARKER DATA

(71) Applicant: Hitachi, Ltd., Tokyo (JP)

(72) Inventors: Georgios Chalkidis, Cottonwood Heights, UT (US); Shinji Tarumi, Salt Lake City, UT (US)

(73) Assignee: HITACHI, LTD., Tokyo (JP)

( * ) Notice: Subject to any disclaimer, the term of this patent is extended or adjusted under 35 U.S.C. 154(b) by 931 days.

(21) Appl. No.: 16/366,753

(22) Filed: Mar. 27, 2019

(65) Prior Publication Data

US 2020/0311612 A1 Oct. 1, 2020

(51) Int. Cl.
  *G16H 20/10* (2018.01)
  *G06N 20/20* (2019.01)
  *G16H 50/20* (2018.01)
  *G06N 5/04* (2006.01)

(52) U.S. Cl.
  CPC ............... *G06N 20/20* (2019.01); *G06N 5/04* (2013.01); *G16H 50/20* (2018.01)

(58) Field of Classification Search
  CPC ...................................................... G06F 3/017
  See application file for complete search history.

(56) References Cited

U.S. PATENT DOCUMENTS

| 10,468,142 | B1* | 11/2019 | Abou Shousha | G16H 30/20 |
| 2013/0185231 | A1* | 7/2013 | Baras | G16H 50/50 706/12 |
| 2014/0058738 | A1 | 2/2014 | Yeskel | |
| 2015/0227701 | A1* | 8/2015 | Nicolaas | G16H 50/20 705/2 |
| 2020/0176113 | A1* | 6/2020 | Megerian | G16H 50/70 |

* cited by examiner

*Primary Examiner* — Di Xiao
(74) *Attorney, Agent, or Firm* — Procopio, Cory, Hargreaves & Savitch LLP

(57) ABSTRACT

Example implementations described herein are directed to the problem of dynamically extracting valid sets of clinical treatments and predictive features from electronic health records to construct models that can predict the effect of treatments and hence compare the effect of multiple, putative treatments. By utilizing a data pipelining technique for constructing machine learning models that only utilizes sets of valid treatment options instead of all possible options, the hardware and computational resources required for constructing the machine learning models can thereby be reduced, and the predicted treatment transition outcomes can be traced to valid treatments, thereby allowing the clinician to understand the effects from a clinical perspective.

15 Claims, 13 Drawing Sheets

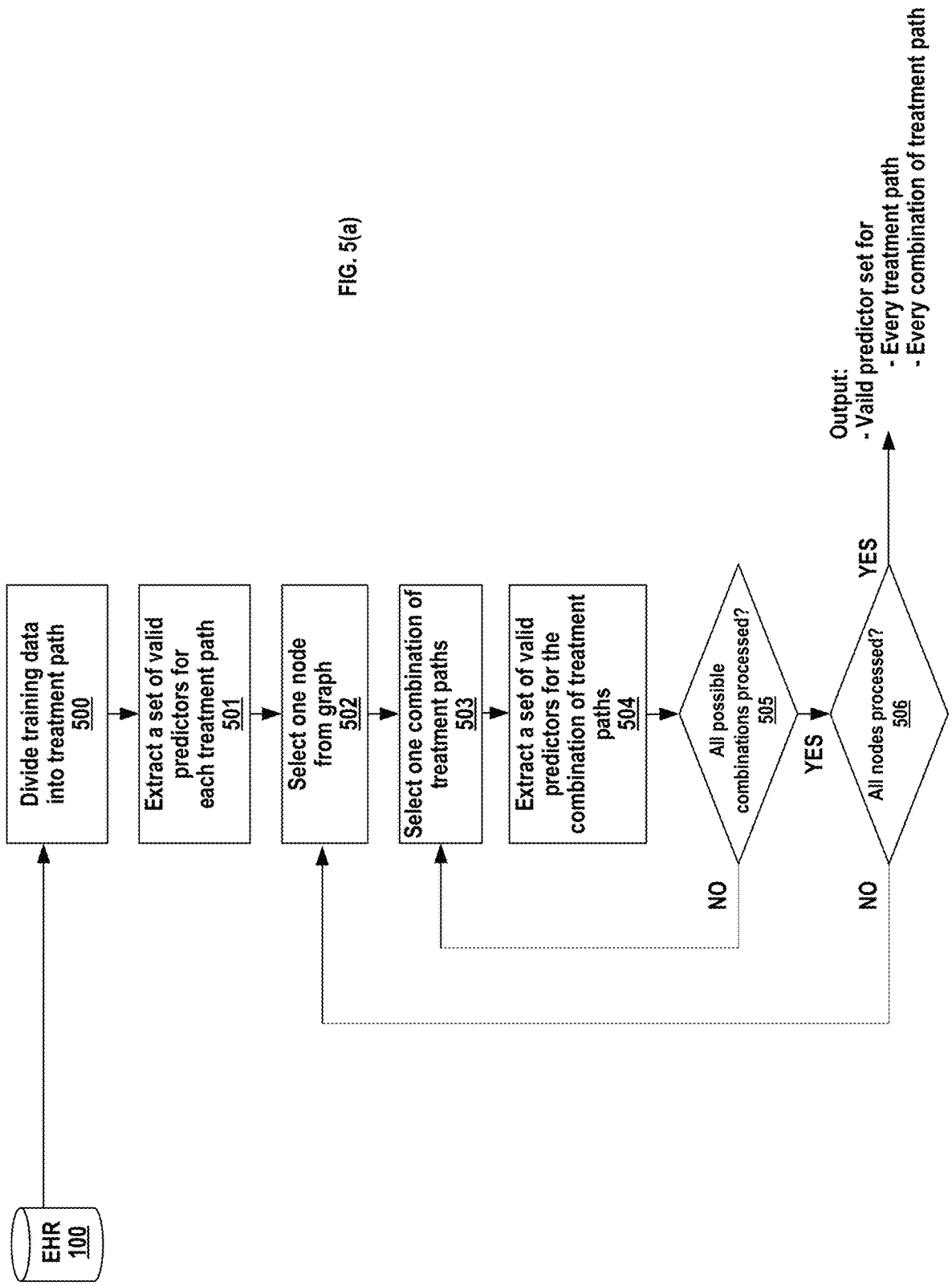

| Path | Demographic | Lab results | Vital results | Diagnosis code |
|---|---|---|---|---|
| A→B | Age, Gender | HbA1c, eGFR | BMI, Blood pressure,... | ••• |
| A→C | Age | HbA1c, eGFR | Blood pressure,... | ••• |
| A→D | Age, Gender | HbA1c | BMI, Blood pressure,... | ••• |
| B→X | | | | |
| B→Y | | | | |
| ••• | | | | |

| Combination of path | Demographic | Lab results | Vital results | Diagnosis code |
|---|---|---|---|---|
| A→B, A→C | Age | HbA1c, eGFR | Blood pressure,... | |
| A→B, A→D | Age, Gender | HbA1c | BMI, Blood pressure,... | |
| A→B, A→C, A→D | Age | HbA1c | Blood pressure,... | |
| B→X, B→Y | | | | |
| ••• | | | | |

FIG. 6(a)

| Path | Target Combination | Model |
|---|---|---|
| A→B | A→B | Model_A_B (pointer to model object) |
| A→C | A→C | Model_A_C |
| A→D | A→D | Model_A_D |
| ... | | |
| A→B | A→B, A→C | Model_A_B_for_BC |
| A→B | A→B, A→D | Model_A_B_for_BD |
| A→B | A→B, A→C, A→D | Model_A_B_for_BCD |
| A→C | A→B, A→C | Model_A_C_for_BC |
| ... | | |

- Models to be used when a user predicts the result of one treatment option
- Models to be used when a user compares more than one option

FIG. 8

SYSTEM FOR PREDICTION MODEL MANAGEMENT WITH TREATMENT PATHWAYS AND BIOMARKER DATA

BACKGROUND

Field

The present disclosure is generally related to machine learning techniques, and more specifically, for machine learning techniques to manage a prediction model with treatment pathways and biomarker data.

Related Art

In related art implementations, applying machine learning (ML) to healthcare data for predicting the effect of treatments and hence comparing the effect of multiple, putative treatments leads to the following problems:

1) Set of clinically valid treatment comparison options is not known a priori
2) Set of clinically valid prediction features dynamically changes as it depends on the data and 1)
3) Selecting the appropriate model for predicting and comparing effects of treatments depends on 1) and 2)

Consequently, without a proper data pre-processing pipeline and model management, ML yields clinically doubtful results and clinically impractical recommendations are being made. Specifically, such ML implementations in the related art can generate results that a clinician cannot recommend, as the clinician cannot determine how such results were determined, and the results may not make sense from a human perspective. As such, even if such recommendations are correct, the recommendation cannot be made by the clinician as no human-level justification can be provided to make such a recommendation.

In the related art for determining medical treatment pathways, there are implementations that involve a method for predictive analytics for medical treatment pathways that are constructed solely on the basis of clinical guidelines.

SUMMARY

In managing type-2 diabetes clinicians are faced with multiple treatment options for a patient and it is not clear at the outset which of those treatments will be most effective and what other possible treatment options are suitable.

From analyzing Electronic Health Records (EHR), baseline HbA1c levels and current treatment type are necessary to stratify patients and predict treatment transition outcome. Although other features affect treatment transition outcomes, HbA1c and current treatment type exert a strong influence.

However, given the status of a patient, it is not obvious which treatments might be suitable and what the potential treatment success rates would be.

Consequently, example implementations are directed to a system that can automatically construct a treatment pathway graph from EHR data provided by a healthcare institution that can support stratification of patients based on their current treatment and HbA1c level. Utilizing this treatment pathway graph, the system can provide adequate treatment options for the patient at hand based on past decisions made by clinicians of the healthcare institution.

Moreover, example implementations described herein can extract valid predictors to predict treatment transition outcome for each patient stratum and construct a treatment transition outcome prediction model for each treatment option. By using these models, a user can compare the personalized treatment transition outcome predicted on the basis of past similar cohort with valid predictors.

Aspects of the present disclosure can involve a method, which involves conducting data pipelining for generating machine learning models for predicting treatment transition outcomes, the method involving generating a treatment pathway graph; extracting one or more sets of valid treatment options from the treatment pathway graph; and extracting valid predictors from the treatment pathway graph.

Aspects of the present disclosure can involve a non-transitory computer readable medium, storing instructions for executing a process which involves conducting data pipelining for generating machine learning models for predicting treatment transition outcomes, the method involving generating a treatment pathway graph; extracting one or more sets of valid treatment options from the treatment pathway graph; and extracting valid predictors from the treatment pathway graph.

Aspects of the present disclosure can involve a system, which involves means for conducting data pipelining for generating machine learning models for predicting treatment transition outcomes, means for generating a treatment pathway graph; means for extracting one or more sets of valid treatment options from the treatment pathway graph; and means for extracting valid predictors from the treatment pathway graph.

Aspects of the present disclosure can involve an apparatus, which involves a process configured to conduct data pipelining for generating machine learning models for predicting treatment transition outcomes, by generating a treatment pathway graph; extracting one or more sets of valid treatment options from the treatment pathway graph; and extracting valid predictors from the treatment pathway graph.

BRIEF DESCRIPTION OF DRAWINGS

FIG. 5(a) illustrates an example of a flow for extracting sets of valid predictors for each treatment path and/or each possible combination of treatment paths in accordance with an example implementation.

FIG. 6(a) illustrates an example of valid predictor sets and a combination of paths, in accordance with an example implementation.

FIG. 8 illustrates an example of a prediction model management table, in accordance with an example implementation.

DETAILED DESCRIPTION

Figure 1:
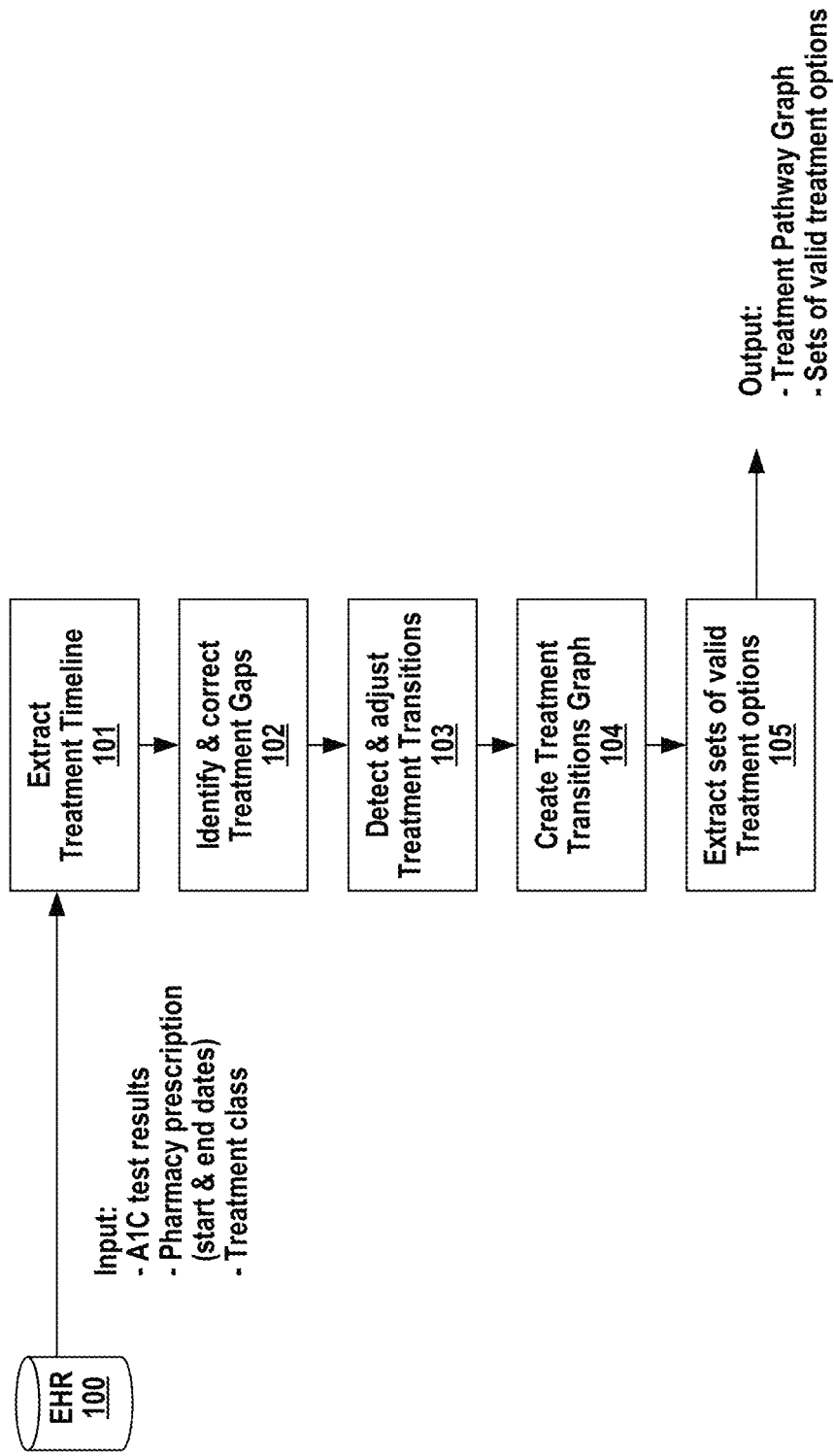
FIG. 1 illustrates an example flow for treatment pathway graph construction, in accordance with an example implementation.

The following detailed description provides further details of the figures and example implementations of the present application. Reference numerals and descriptions of redundant elements between figures are omitted for clarity. Terms used throughout the description are provided as examples and are not intended to be limiting. For example, the use of the term "automatic" may involve fully automatic or semi-automatic implementations involving user or administrator control over certain aspects of the implementation, depending on the desired implementation of one of ordinary skill in the art practicing implementations of the present application. Selection can be conducted by a user through a user interface or other input means, or can be implemented through a desired algorithm. Example implementations as described herein can be utilized either singularly or in combination and the functionality of the example implementations can be implemented through any means according to the desired implementations.

Example implementations are directed to addressing the problems in the related art through 1) automatically extracting sets of allowable clinical treatments from Electronic Health Records (EHR)

2) creating a treatment transition pathway graph stored in a data structure from 1) and user input 3) dynamically extracting sets of clinically valid prediction features based on 1), 2), and user input 4) performing model selection with appropriate treatment logic In managing type 2 diabetes, clinicians look at the HbA1c value of a patient, which measures the blood sugar concentration over the past several months. If the value is greater than some threshold (e.g., 7%), it is said that this patient is diabetic and may undergo adverse health consequences. Thus, some sort of treatment, e.g. lifestyle change, weight loss, anti-diabetic medication, or combinations of the aforementioned, needs to be prescribed that lowers the blood sugar levels of the patient below 7%. Further, in managing type 2 diabetes, in addition to lifestyle changes, including weight loss, there are several potential anti-diabetic medications that a physician can choose to lower HbA1c levels and it is not clear which treatment will yield the best results in terms of lowering HbA1c. Further, since each treatment affects a patient differently on a person-by-person basis, there are several features in the EHR that could be used to help a clinician predict the effect of each treatment and then choose, together with the patient in a shared decision making process, the treatment that has the highest potential of lowering HbA1c levels.

Example implementations are directed to a ML based pharmacotherapy decision support system that can be integrated in a hospital or with insurance companies, depending on the desired implementation. Example implementations start by creating a treatment pathway graph which involves facilitating an interface for the user to limit the prediction algorithms to clinically valid decisions, which is extracted automatically from EHR data as opposed to being based on clinical guidelines alone. As such, example implementations differ from the related art through examining the actual treatment choices that physicians have made in the past, which facilitates the possibility to discover further treatment options that are outside of standard clinical guidelines. Example implementations involving user or administrator control allow manual treatment pathway graph adjustments.

Further, example implementations train an ML implementation by first extracting a set of valid treatments, and for each of such treatments, sets of valid predictors are also extracted that can be then provided for training the ML model.

From the example implementations described herein, the estimate of the average treatment effect can thereby be made closer to what clinicians expect from their experience and also what has been published in clinical trials. In example implementations that utilize the treatment pathway graph with the sets of valid treatment options, an improvement can be made in such estimations over related art ML methods in which a decision tree learning algorithm is applied to all data, which results in treatment effect predictions that do not correspond to what clinicians expected and therefore cannot be recommended by clinicians as there is no way to determine from a human standpoint how such predictions were made.

Further, example implementations result in an improvement over related art ML methods in that predictions of treatment effects from transitions between one treatment and another can thereby be determined. Through the construction of prediction models and input through the example implementations described herein, the prediction models can be integrated with the treatment pathway graph.

In example implementations, valid predictors are extracted for each node in the treatment pathway graph, which can change dynamically depending on what kind of patient the physician is seeing, what kind of treatment the patient is on, and depending on the clinician input. Through the extraction of valid predictors, example implementations determine which treatments should be compared and provide the options that a physician would like to see and compare.

FIG. 1 illustrates an example flow for treatment pathway graph construction, in accordance with an example implementation. Specifically, FIG. 1 illustrates the overall flow to extract the set of all clinically valid treatment options from an EHR data warehouse via patient-provider units to provide the treatment pathway graph and sets of valid treatment options.

At first, the system intakes input data from an EHR electronic data warehouse 100, which can include HbA1c test results from the patients, the treatment history (e.g., pharmacy prescriptions including their start and end dates), and also what kind of diabetes treatments were used (e.g., treatment class). At 101, the system extracts the treatment timeline, which is conducted by creating a continuous treatment timeline.

In the case of type 2 diabetes, which is used as an example and in no way limits the scope of this example implementation, based on available EHR data, such as HbA1c laboratory test results, prescribed treatments, type of treatment etc., a continuous treatment timeline is created in accordance with a desired implementation.

At 102, the system conducts identification and correction of treatment gaps that arise in the treatment history. At 103, the system detects and adjusts treatment conditions, as during transitions between treatment conditions, treatment option overlap can occur, which can result in the extraction of invalid treatment options without proper adjustment. At 104, the system creates a treatment transitions graph, which is then used at 105 for extracting sets of valid treatment options for each patient. As illustrated in FIG. 1, the input of the algorithm includes the medication history and other data available in an EHR data warehouse, and the output is the treatment pathway graph that was extracted. Further, depending on patient characteristics, the sets of valid treatment options that are available to the particular patient are also provided as output.

In an example involving diabetes, example information that is extracted and processed through the flow of FIG. 1 can include, but is not limited to, HbA1c test results, pharmacy prescription information, lab results, and demographic information. The output in such cases can include the sets of clinically valid treatment comparison options, as well as the sets of clinically valid prediction features and a model selection with treatment logic. Further details of each of the processes are provided below.

Figure 2:
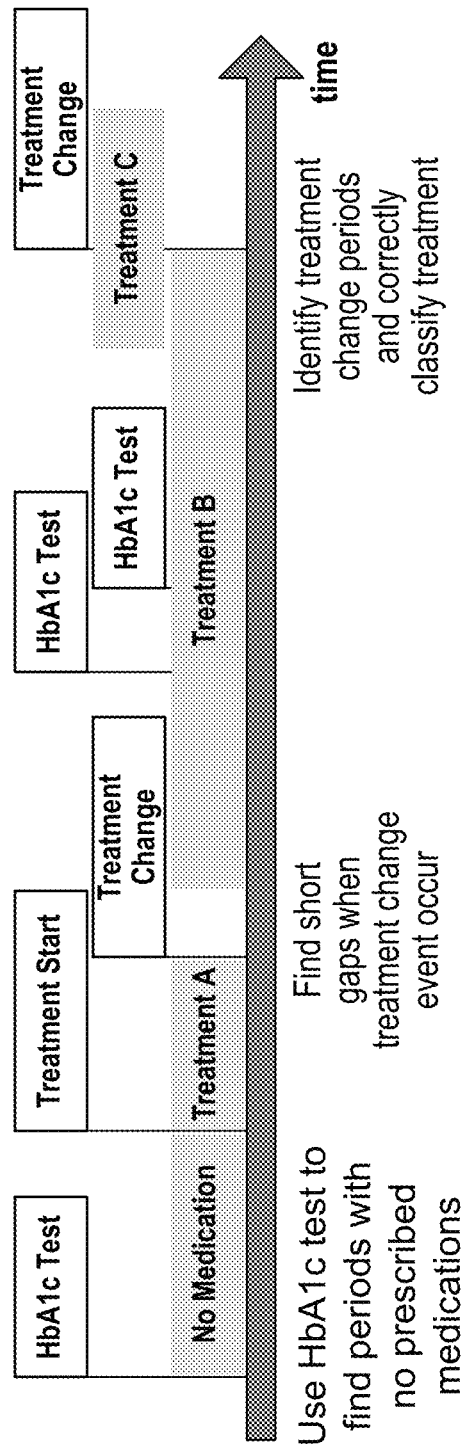
FIG. 2 illustrates an example of a treatment timeline, in accordance with an example implementation.

FIG. 2 illustrates an example of a treatment timeline, in accordance with an example implementation. Specifically, FIG. 2 illustrates an example of diabetes related events provided from the EHR which will be later used for graph constructions. Such events can include treatment change events and HbA1c tests, which are utilized in order to capture when patients are on or off anti-diabetic medications. As illustrated in the time line of FIG. 2, the system creates the treatment timeline from which the treatment pathway graph is constructed through three aspects. In a first aspect, the system identifies treatment pathway gaps that arise due to small time delays between treatments when e.g. new medications are being prescribed. In a second aspect, the algorithm detects treatment transition events to identify the final treatment option. In a third aspect the system produces start-end intervals with no unaccounted gaps for the treatment pathway graph.

In the example shown in FIG. 2, HbA1c tests are labeled along the time line to determine periods of time in which no medications (No Med) are taken by the patient. Based on the start and end dates of prescriptions, treatment changes are labeled for the short gaps in which a treatment change event occurs. Further, when there are overlapping treatments as determined from the start and stop dates of treatments, the system identifies when treatment change periods occur so the treatment can be correctly classified. From such classifications, the sets of valid treatment options can be determined across all of the patients in the database, which encompass the transitions between treatments made across all of the patients. Such information is then utilized to generate a treatment pathway graph as illustrated in FIG. 3.

Figure 3:
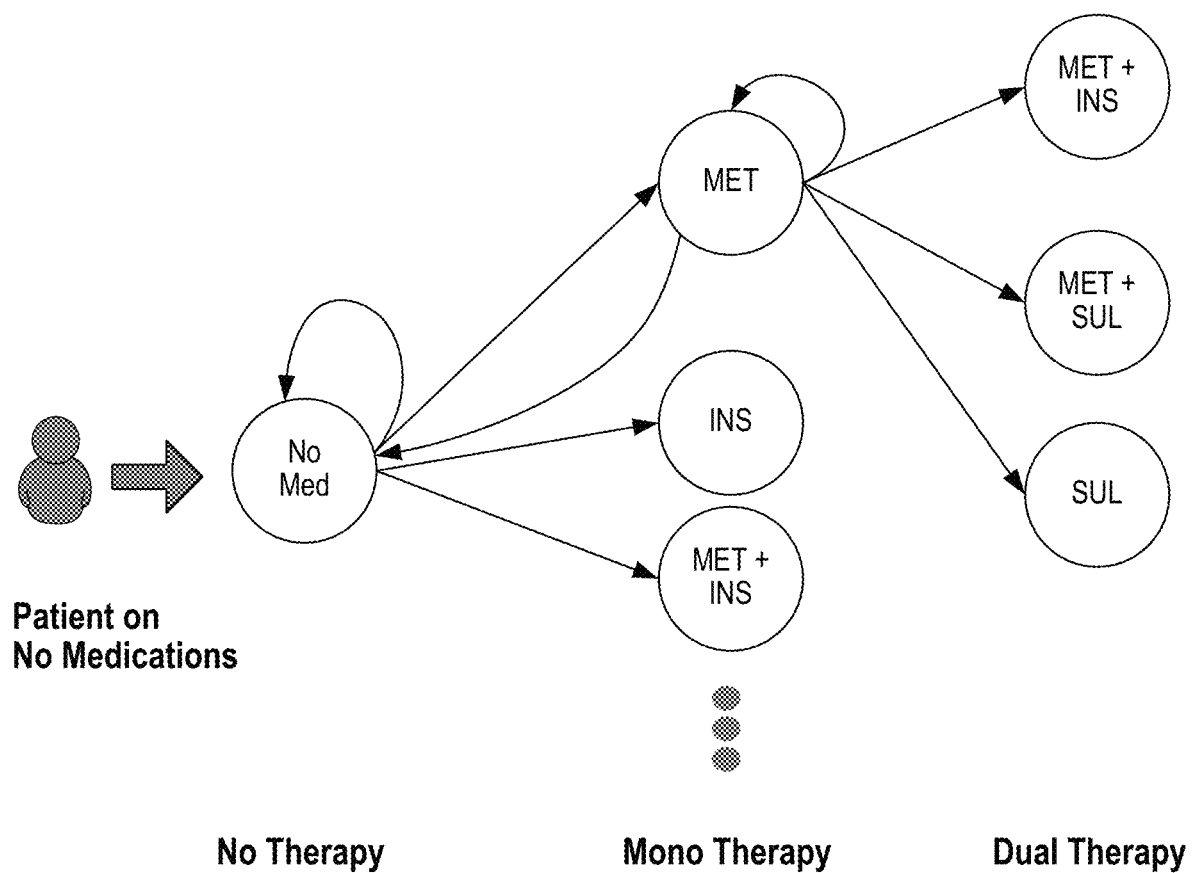
FIG. 3 illustrates an example of a treatment pathway graph, in accordance with an example implementation.

FIG. 3 illustrates an example of a treatment pathway graph, in accordance with an example implementation. In the example treatment pathway graph of FIG. 3, each node is indicative of a particular treatment option, and then the arrows indicate the valid pathways between each medication treatment, which are utilized to indicate the sets of valid treatment options as only a limited number of clinical relevant transitions occur in practice. For example, in this case, the node "no med" means no medication (e.g., the patient is not currently taking any anti-diabetic medication), and that the valid treatment pathways can include various treatment nodes such as insulin (INS) or can be continuously maintained as no medication. Thus, example implementations involve a machine learning model for each transition determined from the extracted predictor sets that predicts the treatment effect based on the underlying condition and the valid pathways. In example implementations, machine learning models are constructed through only using the valid treatment options as indicated by the possible transition pathways between nodes as well as by using the valid predictor sets instead of all predictors, which reduces the hardware and computation costs for constructing machine learning models. Further, the treatment effect and valid prediction features change based on the transition direction as defined by the sets of valid treatment options. From the treatment pathway graph of FIG. 3, models can be generated to predict treatment transition outcomes (i.e., moving from one treatment state to another treatment state along the treatment pathway graph).

Figure 4:
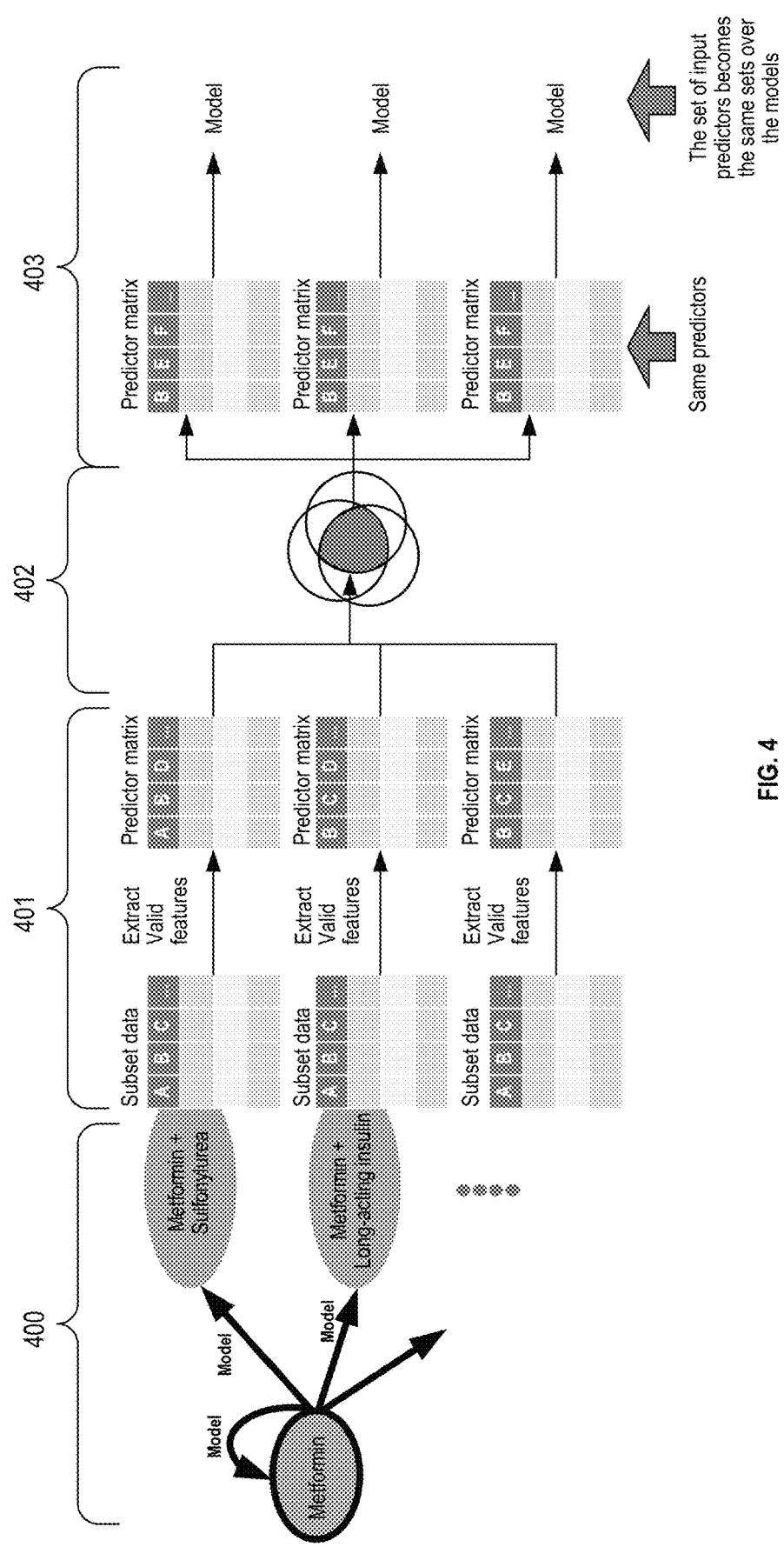
FIG. 4 illustrates an example flow for constructing a treatment transition outcome prediction model, in accordance with an example implementation.

FIG. 4 illustrates an example flow for constructing a treatment transition outcome prediction model, in accordance with an example implementation. The example of FIG. 4 is directed to Metformin, however, example implementations described herein can be extended to any type of treatment option in accordance with the desired implementation.

At 400, the flow defines the treatment options that can be applied to the patient stratum by using the treatment pathway as provided from FIG. 3. In this process, the data sets are divided for each condition path into subset data, which is organized into features as shown in the subset data of FIG. 4 (e.g., A, B, C). Such features can include, but are not limited to, age, gender, disease information, and other information in accordance with the desired implementation.

Figure 5B:
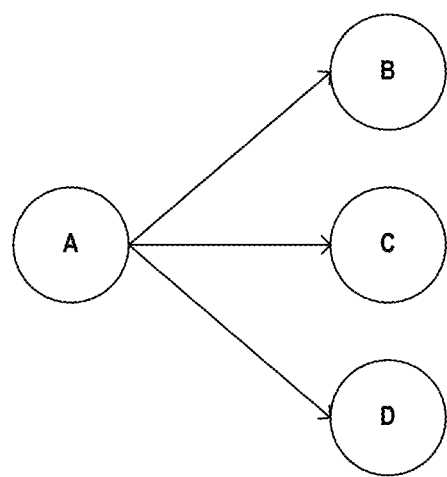
FIG. 5(b) illustrates an example of a treatment graph from which treatment paths can be extracted in accordance with an example implementation.

At 401, the flow proceeds to extract valid predictors using information criterion/statistics for each of the treatment options to create the predictor matrix as illustrated in FIG. 4. At 402, the intersection of all of the set of predictors is extracted to provide an intersected predictor matrix that spans across all of the treatment pathways using the same predictors as illustrated in FIG. 4. Further details of the flow at 401 and 402 are provided with respect to FIGS. 5(a) and 5(b). At 403, the flow constructs a treatment transition outcome prediction model. The set of input predictors becomes the same sets over the models across all of the treatment pathways. In a logical extension this implementation can be generalized to yield a set of universal valid predictors. When executed on the full treatment pathway graph, the flow depicted in FIG. 4 produces a set of universal valid predictors that are applicable to every valid treatment option with respect to the treatment pathway graph.

FIG. 5(a) illustrates an example of a flow for extracting sets of valid predictors for each treatment path and/or each possible combination of treatment paths in accordance with an example implementation. In related art machine learning techniques, all sets of predictors are utilized to construct models on the general premise that more predictors lead to better predictive outcomes. However, such predictors are computationally expensive and can require extensive hardware to implement. Further, even if the resultant model is accurate, the predictors may generate recommendations or predict treatment effects that do not make sense to a physician from a clinical perspective. In such situations, even if the treatment path is effective and/or the predicted treatment effect is correct, the physician cannot recommend the treatment as there is no method to understand on what grounds the treatment is being recommended and how the treatment path was derived.

To address the above problems, example implementations extract valid predictor sets for every treatment path and every combination of treatment paths so that not only can a model be generated to recommend a treatment, but other pathways can be compared with the recommendation to provide alternative options. Further, example implementations reduce the predictor sets to ones that can be utilized by all possible pathways according to sets of valid treatment options (the treatment paths defined in the treatment pathway graph), thereby reducing the computation and hardware needed to generate a machine learning model for constructing the treatment model as the construction is thereby limited to the determined sets of valid treatment options from FIG. 1.

The initial input from the EHR 100 can include the treatment pathway graph as illustrated in FIG. 3 as well as the training data set. Such training data can include, but is not limited to, HbA1c test results, pharmacy prescriptions, start and end dates of the pharmacy prescriptions, treatment class, lab/vital results, and diagnosis codes.

At 500, the flow divides the training data into each treatment path.

At 501, the flow extracts a set of valid predictors for each treatment path. There are several methods that can be applied to extract the set of valid predictors, such as evaluating metrics of each predictor and extracting the predictors having metrics that are over a predefined threshold in accordance with an example implementation. Such metrics can include the ratio of blanks, correlation with target variables, mutual information with target variables, or other metrics in accordance with the desired implementation. Such metrics are set in accordance with the desired implementation.

At 502, the flow selects one node from the graph, which can involve feature extraction methods such as, but not limited to, stepwise AIC (Akaike information criterion) or LASSO (least absolute shrinkage and selection operator), or any other feature extraction method in accordance with the desired implementation.

At 503, the flow selects one combination of treatment paths. For example, suppose the treatment graph is as illustrated in FIG. 5(*b*). Possible combinations of the graph can include {A→B, A→C}, {A→B, A→C}, and {A→B, A→C, A→D}.

At 504, the flow extracts a set of valid predictors for the combination of treatment paths. This process is accomplished by extracting the intersection of all sets of valid predictors that belong to the selected path combination from the flow at 503.

At 505, a determination is made as to whether all possible combinations of treatment paths as determined from the flow at 503 have been processed for the node. If so (Yes) the flow proceeds to 506, otherwise (No) the flow proceeds back to 503 to select the next combination of treatment paths.

At 506, a determination is made as to whether all of the nodes have been processed. If so (Yes) then the flow provides as an output the valid predictor set for every treatment path as well as every combination of treatment paths. Otherwise (No), the flow proceeds back to 502 to select the next node.

Figure 6B:
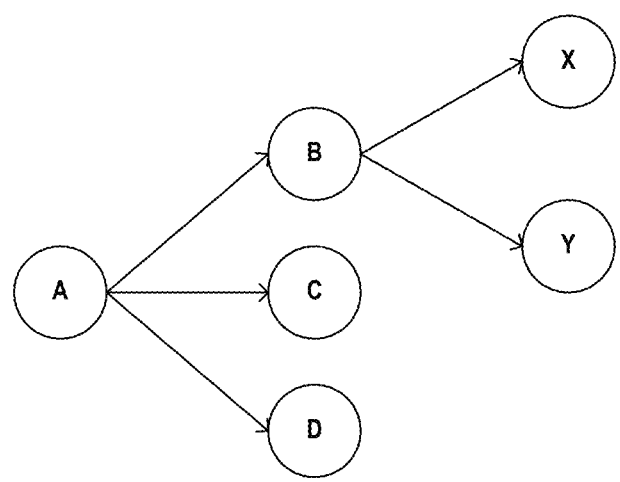
FIG. 6(b) illustrates an example treatment pathway graph for the valid predictor sets of FIG. 6(a).

FIG. 6(*a*) illustrates an example of valid predictor sets and a combination of paths, in accordance with an example implementation. As illustrated, the valid predictor set for every treatment path involves a path, demographic information, lab results, vital results, diagnosis code, and other data according to the desired implementation. The valid predictor set for every combination of treatment path involves all combinations of paths, demographics, lab results, vital results, diagnosis code, and other data according to the desired implementation. By utilizing the possibility of every combination of treatment path, the process for generating models receives the same predictor set and predicts each treatment transition outcome for each treatment path. As illustrated in FIG. 5(*a*), the first loop is directed to node processing and the second loop is directed to combinations of treatment paths. By executing the process to generate valid predictor sets for every treatment path and every combination of treatment paths, example implementations can thereby construct prediction models for comparisons between different treatment paths. For example, if one node is linked to three different treatment paths, the known treatment can be linked.

In example implementations, there are situations in which the clinician sometimes wants to compare only two options, such as no treatment transitioning to Metformin versus insulin. There can be many such possible combinations of interest to the clinician. From the example of FIG. 6(*b*), assume that the path from A to B has age and gender as valid predictors and paths from A to C has only age as valid predictors. In this case, the combination from A to B path and from A to C path has only age as a valid predictor. That is because gender is a valid predictor for A to B but it is not valid for A to C so, in this case, the flow for extracting the intersection of predictors determines that the combination A to B and A to C has only age as valid predictors, as illustrated in FIG. 6(*a*).

Figure 7:
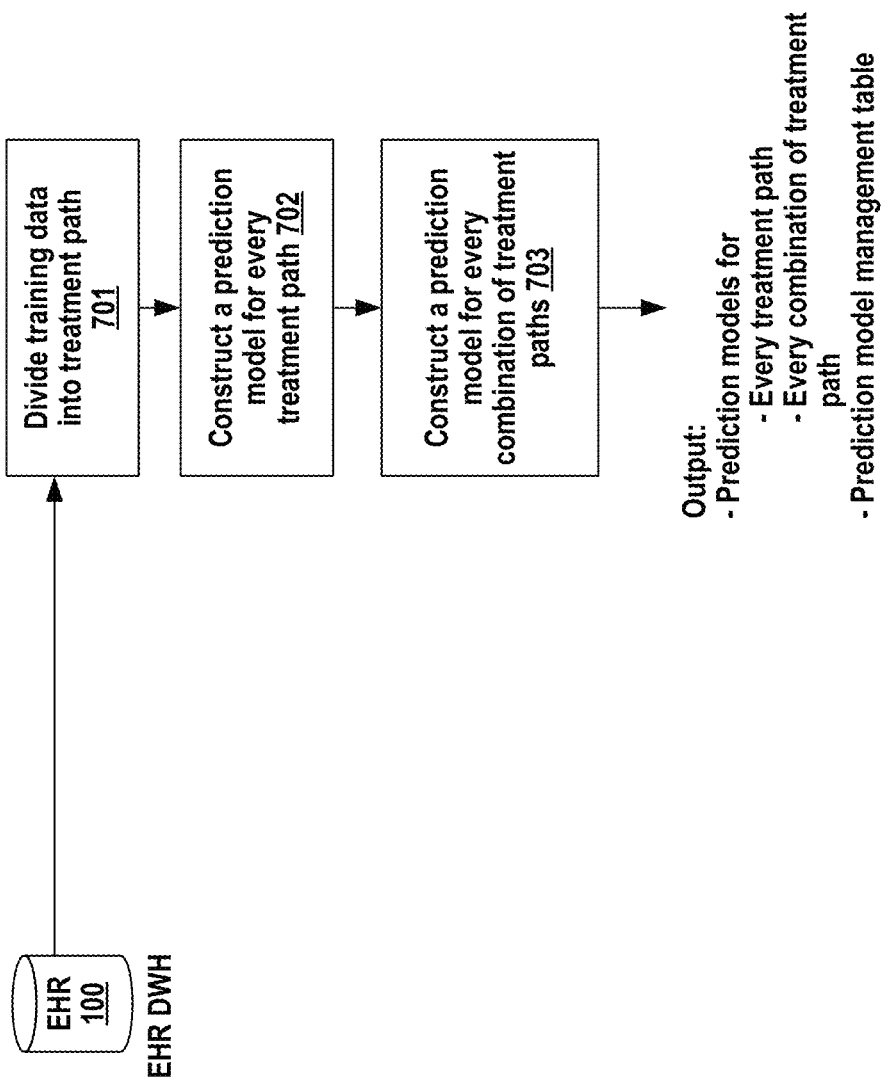
FIG. 7 illustrates an example flow to construct prediction models for each treatment path and each combination of treatment paths in accordance with an example implementation.

FIG. 7 illustrates an example flow to construct prediction models for each treatment path and each combination of treatment paths in accordance with an example implementation. In example implementations, the input can involve the treatment pathway graph and the training data set as described with respect to FIG. 5(*a*), as well as the output valid predictor set for every treatment path and every combination of treatment paths generated from the flow of FIG. 5(*a*) and as illustrated in FIG. 6(*a*).

At 701, the flow divides the training data into the treatment paths.

At 702, the flow constructs a prediction model for every treatment path 702. The prediction models can be constructed by using the divided training data on the treatment path as well as the valid predictor set linked to the treatment path. Such machine learning techniques can be constructed according to any implementation in the related art.

At 703, the flow constructs a prediction model for every combination of treatment paths. The prediction models can be constructed by using the divided training data on the treatment path as well as the valid predictor set linked to the combination of treatment paths. As a result, there are generated prediction models for every treatment path and every combination of treatment paths as well as a prediction model management table that manages the generated prediction models as illustrated in FIG. 8.

FIG. 8 illustrates an example of a prediction model management table, in accordance with an example implementation. As illustrated in FIG. 8, the model management table contains models to be used when a clinician predicts the result of one treatment option, and models to be utilized when the clinician compares more than one option.

As illustrated in the above, example implementations extract a valid predictor set for all possible combinations of valid treatment paths so the output of the process is a valid predictor set for every treatment path and every combination of a treatment path, which is used to construct the models as illustrated in FIG. 8. Through the example implementations, if a clinician wants to compare the treatment paths (e.g., A to B and A to C), then the clinician can do so through the combination of treatment path models. Through such example implementations, clinicians can traverse through individual treatment paths through models that provide predictions for the treatment option, as well as direct comparisons of predictions in comparing multiple treatment paths.

Further, due to the processes used in example implementations to be directed to only valid prediction sets, the models provide predictions that can be traversed through their treatment path in a manner that would make sense to a clinician and thereby be recommendable. In addition, because the valid prediction sets used to generate the model reduce the amount of data utilized in machine learning algorithms, the example implementations can generate models faster than related art implementations and require less hardware. Such example implementations are useful in environments such as hospitals, which do not typically have high end hardware like related art cloud systems dedicated to machine learning processes, and also such data cannot normally be easily provided to a third-party cloud vendor due to regulatory compliance issues.

Figure 9:
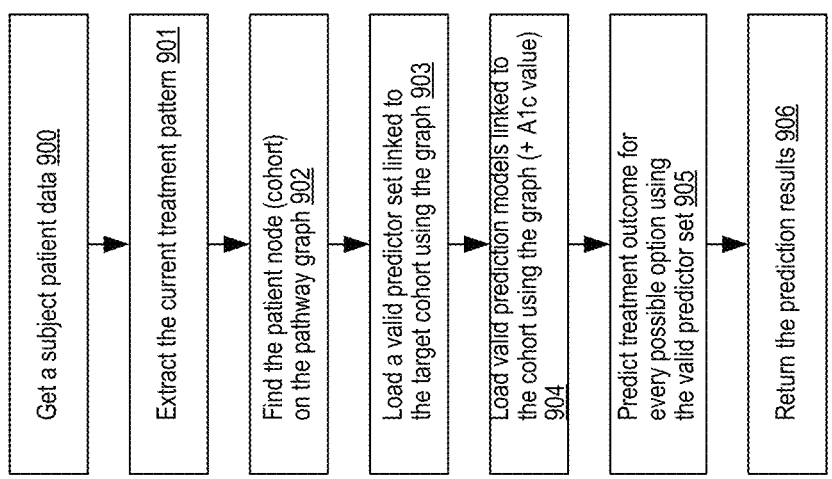
FIG. 9 illustrates an example flow for model management, in accordance with an example implementation.

FIG. 9 illustrates an example flow for model management, in accordance with an example implementation. Specifically, FIG. 9 illustrates the flow for model management processing in which each treatment path is linked to each prediction model, and each node (cohort) linked to a valid predictor set can thereby be used to the linked models. At 900, the flow obtains data regarding a subject patient from the database. At 901, the flow extracts the current treatment pattern. At 902, the flow determines the patient node (cohort) on the pathway graph. At 903, the flow loads a valid predictor set linked to the target cohort using the graph. At 904, the flow loads the valid prediction models linked to the cohort using the graph. At 905, the flow predicts the treatment transition outcome for every possible option using the valid predictor set. At 906, the predicted treatment transition outcomes are then returned.

Figure 10:
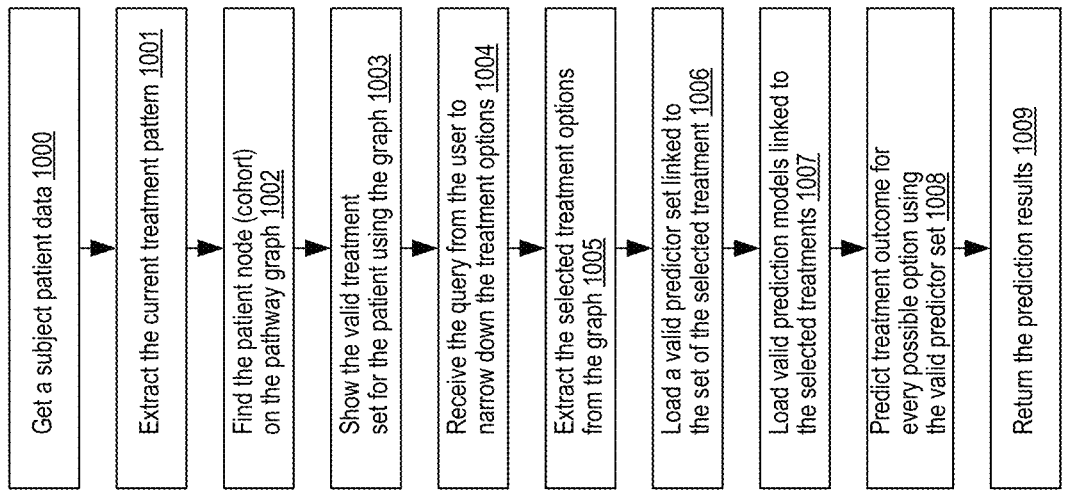
FIG. 10 illustrates another example flow for model management, in accordance with an example implementation.

FIG. 10 illustrates another example flow for model management, in accordance with an example implementation. Specifically, FIG. 10 illustrates a flow in which each treatment path is linked to each prediction model, and each node (cohort) linked to a valid predictor set can be used to the linked models. At 1000, the subject patient data is obtained. At 1001, the current treatment pattern is extracted. At 1002, the flow finds the patient node (cohort) on the pathway graph. At 1003, the flow shows the valid treatment option set from the sets of valid treatment options for the patient using the graph. At 1004, the flow receives a query from the clinician to narrow down the treatment options. At 1005, the flow extracts the selected treatment options from the graph. At 1006, the flow loads a valid predictor set linked to the set of the selected treatment. At 1007, the flow loads valid prediction models linked to the selected treatments. At 1008, the flow predicts treatment transition outcomes for every possible option using the valid prediction set. At 1009, the flow returns the predicted treatment transition outcomes.

FIGS. 9 and 10 can be implemented to provide an interface whereupon a clinician can utilize the machine learning models for predicting treatment transition outcomes for a given subject patient through providing subject patient data and executing the flows therein. Through such example implementations, the clinician can thereby compare predicted outcomes between treatment transition options (e.g., between no medication to insulin versus no medication to Metformin).

Figure 11:
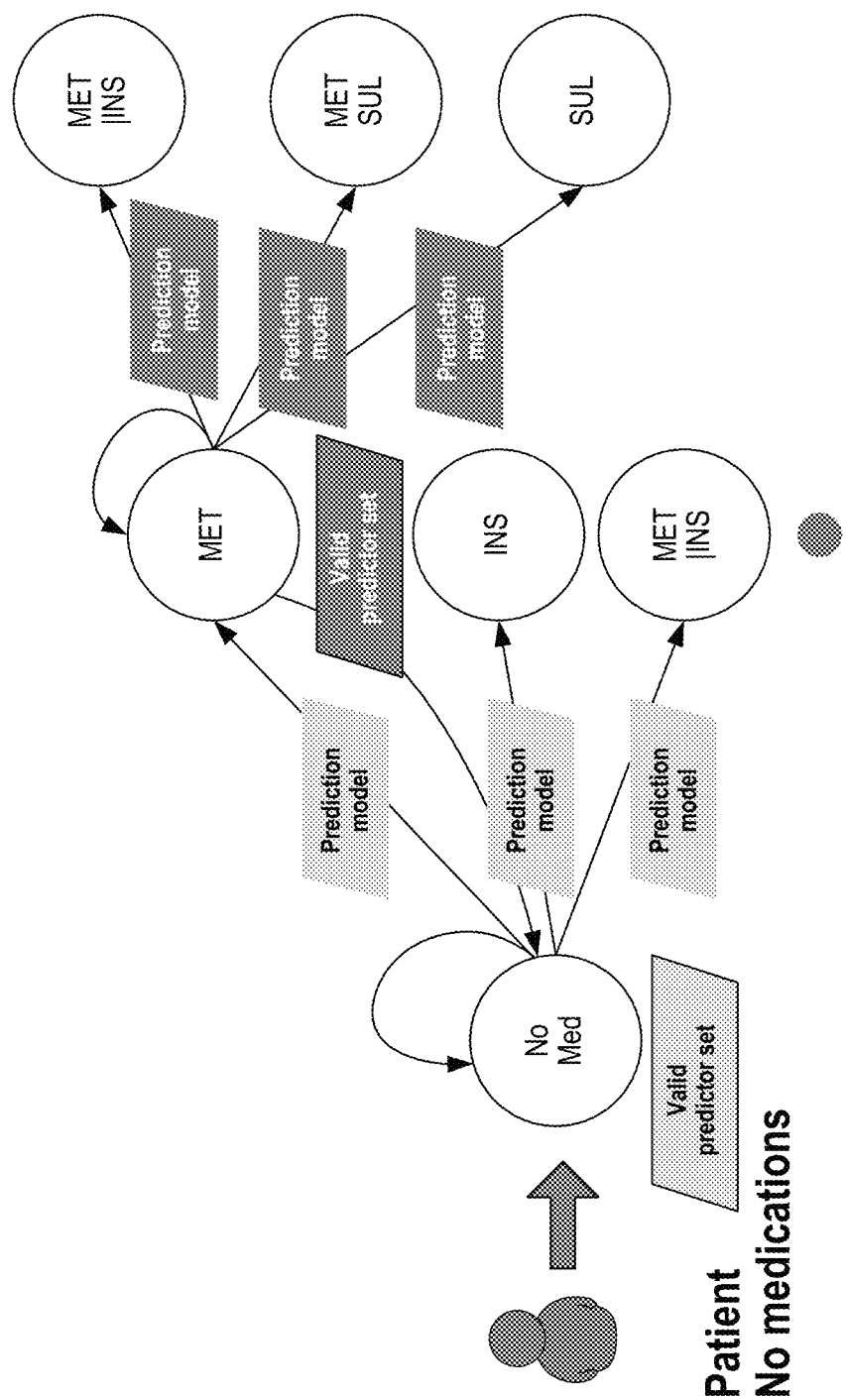
FIG. 11 illustrates an example output of the treatment graph with valid predictor sets and prediction models, in accordance with an example implementation.

FIG. 11 illustrates an example output of the treatment graph with valid predictor sets and prediction models, in accordance with an example implementation. In example implementations, each treatment path is linked to each prediction model, and each node is linked to a valid predictor set that can be used to the linked models, whereupon the flows of FIGS. 9 and 10 can be used to generate predictions based on the treatment graph of FIG. 11. In this manner, the valid predictor set indicates the set of valid predictions that can occur from a treatment, and the prediction models can be interposed in transitions between treatment options, whereupon the corresponding machine learning model provides the results regarding the treatment effects when transitioning from one treatment to another.

Thus, as described in example implementations, in a first aspect there is a treatment pathway graph construction process, a valid treatment comparison set extraction process and a valid predictor set extraction process as described with respect to FIGS. 1 to 6(b). In this example implementation, each of the cohort's EHR records, the valid predictors of which were extracted in advance, can be linked to the path of the treatment graph. Outcome estimation can be performed by patient similarity matching based on the valid predictors.

In a second aspect as described with respect to FIGS. 7 to 11, there is a prediction model construction process and a prediction model management process. In this manner, the treatment pathways are associated with a prediction management as illustrated in FIG. 8 for a graph as illustrated in FIG. 11.

Figure 12:
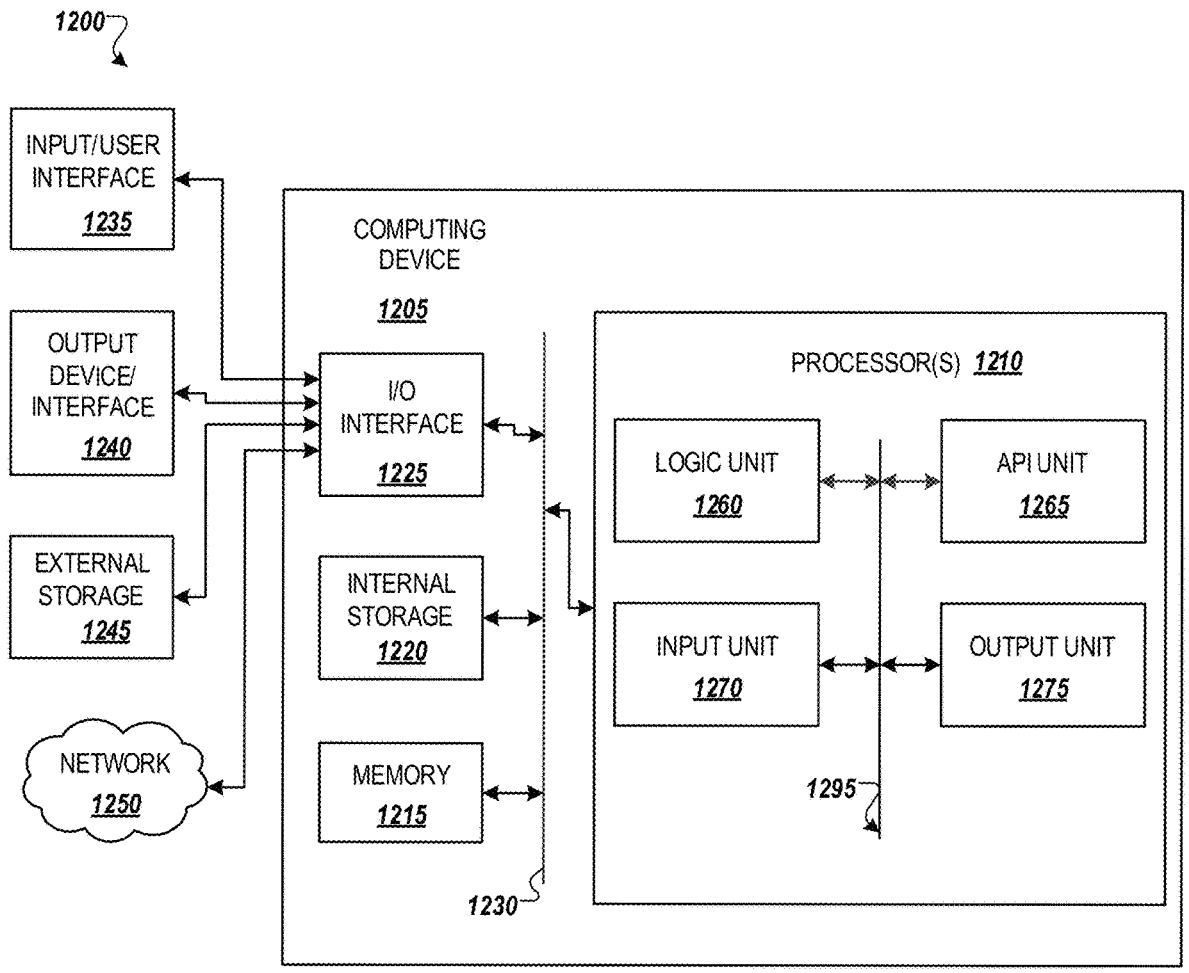
FIG. 12 illustrates an example computing environment with an example computer device suitable for use in example implementations.

FIG. 12 illustrates an example computing environment with an example computer device suitable for use in example implementations. Computer device 1205 in computing environment 1200 can include one or more processing units, cores, or processors 1210, memory 1215 (e.g., RAM, ROM, and/or the like), internal storage 1220 (e.g., magnetic, optical, solid state storage, and/or organic), and/or I/O interface 1225, any of which can be coupled on a communication mechanism or bus 1230 for communicating information or embedded in the computer device 1205.

Computer device 1205 can be communicatively coupled to input/user interface 1235 and output device/interface 1240. Either one or both of input/user interface 1235 and output device/interface 1240 can be a wired or wireless interface and can be detachable. Input/user interface 1235 may include any device, component, sensor, or interface, physical or virtual, that can be used to provide input (e.g., buttons, touch-screen interface, keyboard, a pointing/cursor control, microphone, camera, braille, motion sensor, optical reader, and/or the like). Output device/interface 1240 may include a display, television, monitor, printer, speaker, braille, or the like. In some example implementations, input/user interface 1235 and output device/interface 1240 can be embedded with or physically coupled to the computer device 1205. In other example implementations, other computer devices may function as or provide the functions of input/user interface 1235 and output device/interface 1240 for a computer device 1205. In example implementations involving a touch screen display, a television display, or any other form of display, the display is configured to provide a user interface.

Examples of computer device 1205 may include, but are not limited to, highly mobile devices (e.g., smartphones, devices in vehicles and other machines, devices carried by humans and animals, and the like), mobile devices (e.g., tablets, notebooks, laptops, personal computers, portable televisions, radios, and the like), and devices not designed for mobility (e.g., desktop computers, other computers, information kiosks, televisions with one or more processors embedded therein and/or coupled thereto, radios, and the like).

Computer device 1205 can be communicatively coupled (e.g., via I/O interface 1225) to external storage 1245 and network 1250 for communicating with any number of networked components, devices, and systems, including one or more computer devices of the same or different configuration. Computer device 1205 or any connected computer device can be functioning as, providing services of, or referred to as a server, client, thin server, general machine, special-purpose machine, or another label.

I/O interface 1225 can include, but is not limited to, wired and/or wireless interfaces using any communication or I/O protocols or standards (e.g., Ethernet, 802.11x, Universal System Bus, WiMax, modem, a cellular network protocol, and the like) for communicating information to and/or from at least all the connected components, devices, and network in computing environment 1200. Network 1250 can be any network or combination of networks (e.g., the Internet, local area network, wide area network, a telephonic network, a cellular network, satellite network, and the like).

Computer device 1205 can use and/or communicate using computer-usable or computer-readable media, including transitory media and non-transitory media. Transitory media include transmission media (e.g., metal cables, fiber optics), signals, carrier waves, and the like. Non-transitory media include magnetic media (e.g., disks and tapes), optical media (e.g., CD ROM, digital video disks, Blu-ray disks), solid state media (e.g., RAM, ROM, flash memory, solid-state storage), and other non-volatile storage or memory.

Computer device 1205 can be used to implement techniques, methods, applications, processes, or computer-executable instructions in some example computing environments. Computer-executable instructions can be retrieved from transitory media, and stored on and retrieved from non-transitory media. The executable instructions can originate from one or more of any programming, scripting, and machine languages (e.g., C, C++, C#, Java, Visual Basic, Python, Perl, JavaScript, and others).

Memory 1215 may be configured to store or manage algorithms to be executed by processor(s) 1210 as described in the flow, for example, of FIGS. 1, 4, 5(*a*), 7, 9 and 10. The example implementations as described herein may be conducted singularly, or in any combination of each other according to the desired implementation and are not limited to a particular example implementation. Memory 1215 may also manage the management information as illustrated in FIG. 6(*a*) and FIG. 8, as well as the treatment pathway graphs as and timelines as illustrated in FIGS. 2-4 and 11.

Processor(s) 1210 can execute under any operating system (OS) (not shown), in a native or virtual environment. One or more applications can be deployed that include logic unit 1260, application programming interface (API) unit 1265, input unit 1270, output unit 1275, and inter-unit communication mechanism 1295 for the different units to communicate with each other, with the OS, and with other applications (not shown). The described units and elements can be varied in design, function, configuration, or implementation and are not limited to the descriptions provided. Processor(s) 1210 can be in the form of physical processors or central processing units (CPU) that is configured to execute instructions loaded from Memory 1215.

In some example implementations, when information or an execution instruction is received by API unit 1265, it may be communicated to one or more other units (e.g., logic unit 1260, input unit 1270, output unit 1275). In some instances, logic unit 1260 may be configured to control the information flow among the units and direct the services provided by API unit 1265, input unit 1270, output unit 1275, in some example implementations described above. For example, the flow of one or more processes or implementations may be controlled by logic unit 1260 alone or in conjunction with API unit 1265. The input unit 1270 may be configured to obtain input for the calculations described in the example implementations, and the output unit 1275 may be configured to provide output based on the calculations described in example implementations.

In example implementations, processor(s) 1210 execute a process for treatment pathway graph construction, a process for determining valid clinical treatment sets (e.g. sets of valid treatment options), a process for determining valid predictor sets, a process for prediction model construction, and a process for prediction model management. Processor(s) 1210 take in as input EHR data (biomarkers, lab values, demographics, pharmacy prescriptions, and so on), EHR data of a subject patient (when supporting decision) and user specific input (e.g., metrics). In response to the input through the processes as described above, processor(s) 1210 can thereby output sets of clinically valid treatment options for comparison, sets of stratified patients, sets of valid predictors for building prediction models and for comparing treatment options, as well as the predicted treatment transition outcome of each possible valid treatment option.

In example implementations, the process for treatment pathway graph construction and the process for determining valid clinical treatment sets can be utilized as part of treatment pathway graph construction process with a clinically valid treatment options extraction process. Further, processor(s) 1210 can be configured to conduct extraction of a valid feature set for each cohort and construct prediction models, as well as manage such treatment transition outcome prediction models.

Processor(s) 1210 can be configured to conduct data pipelining for generating machine learning models for predicting treatment transition outcomes by generating a treatment pathway graph as illustrated in FIG. 1, extracting one or more sets of valid treatment options from the treatment pathway graph as illustrated in FIG. 1; and extracting valid predictors from the treatment pathway graph as illustrated in FIG. 4 and FIG. 5(*a*).

Processor(s) 1210 can conduct the generating of the treatment pathway graph by extracting a medication timeline from electronic health records; correcting gaps in the medication timeline; detecting medication transitions from the corrected medication timeline; and generating the treatment pathway graph from the medication transitions as illustrated in FIGS. 1 and 2.

Processor(s) 1210 can conduct the extracting of valid predictors from the treatment pathway graph by dividing training data from electronic health records into each treatment path in the treatment pathway graph; extracting first valid predictors from the each treatment path; and for each node in the treatment graph, extracting second valid predictors from all combinations of treatment paths starting from the each node in the treatment pathway graph as illustrated in FIG. 5(*a*) and as shown for FIG. 6(*a*).

Processor(s) 1210 can conduct the generating of the machine learning models for predicting treatment transition outcomes, the generating involving dividing training data from electronic health records into each treatment path in the treatment pathway graph; constructing first machine learning models for predicting treatment transition outcomes for the each treatment path from the first valid predictors; and constructing second machine learning models for predicting treatment transition outcomes for the each treatment path from the second valid predictors as illustrated in FIG. 7 and FIG. 8.

Processor(s) 1210 can also provide an interface whereupon a clinician can utilize the machine learning models for predicting treatment transition outcomes for a given subject patient through providing subject patient data. The process can involve extracting a current treatment pattern from the subject patient data; determining a patient node on the treatment pathway graph; determining associated ones of the one or more sets of valid treatment options based on the patient node; determining ones of the machine learning models for predicting treatment transition outcomes associated with the patient node; executing on the ones of the machine learning models, each of the associated ones of the one or more sets of valid treatment options to predict treatment transition outcomes for all of the associated ones of the one or more sets of valid treatment options; and providing the predicted treatment transition outcomes as illustrated in FIG. 9.

Processor(s) 1210 can also provide an interface whereupon a clinician can utilize the machine learning models for predicting treatment transition outcomes for a given subject patient through providing subject patient data. The process can involve extracting a current treatment pattern from the subject patient data; determining a patient node on the treatment pathway graph; for a selection of a valid treatment option set from the sets of valid treatment options on the treatment pathway graph: extracting selected valid treatment option set from the sets of valid treatment options from the treatment pathway graph; determining associated ones of the one or more sets of valid treatment options based on the extracted selected valid treatment option set from the sets of valid treatment options; determining ones of the machine learning models for predicting treatment transition outcomes associated with the selected valid treatment option set from the sets of valid treatment options; executing on the ones of the machine learning models, each of the associated ones of the one or more sets of valid treatment options to predict treatment transition outcomes for all of the associated ones of the one or more sets of valid treatment options; and providing the predicted treatment transition outcomes as illustrated in FIG. 10.

Some portions of the detailed description are presented in terms of algorithms and symbolic representations of operations within a computer. These algorithmic descriptions and symbolic representations are the means used by those skilled in the data processing arts to convey the essence of their innovations to others skilled in the art. An algorithm is a series of defined steps leading to a desired end state or result. In example implementations, the steps carried out require physical manipulations of tangible quantities for achieving a tangible result.

Unless specifically stated otherwise, as apparent from the discussion, it is appreciated that throughout the description, discussions utilizing terms such as "processing," "computing," "calculating," "determining," "displaying," or the like, can include the actions and processes of a computer system or other information processing device that manipulates and transforms data represented as physical (electronic) quantities within the computer system's registers and memories into other data similarly represented as physical quantities within the computer system's memories or registers or other information storage, transmission or display devices.

Example implementations may also relate to an apparatus for performing the operations herein. This apparatus may be specially constructed for the required purposes, or it may include one or more general-purpose computers selectively activated or reconfigured by one or more computer programs. Such computer programs may be stored in a computer readable medium, such as a computer-readable storage medium or a computer-readable signal medium. A computer-readable storage medium may involve tangible mediums such as, but not limited to optical disks, magnetic disks, read-only memories, random access memories, solid state devices and drives, or any other types of tangible or non-transitory media suitable for storing electronic information. A computer readable signal medium may include mediums such as carrier waves. The algorithms and displays presented herein are not inherently related to any particular computer or other apparatus. Computer programs can involve pure software implementations that involve instructions that perform the operations of the desired implementation.

Various general-purpose systems may be used with programs and modules in accordance with the examples herein, or it may prove convenient to construct a more specialized apparatus to perform desired method steps. In addition, the example implementations are not described with reference to any particular programming language. It will be appreciated that a variety of programming languages may be used to implement the teachings of the example implementations as described herein. The instructions of the programming language(s) may be executed by one or more processing devices, e.g., central processing units (CPUs), processors, or controllers.

As is known in the art, the operations described above can be performed by hardware, software, or some combination of software and hardware. Various aspects of the example implementations may be implemented using circuits and logic devices (hardware), while other aspects may be implemented using instructions stored on a machine-readable medium (software), which if executed by a processor, would cause the processor to perform a method to carry out implementations of the present application. Further, some example implementations of the present application may be performed solely in hardware, whereas other example implementations may be performed solely in software. Moreover, the various functions described can be performed in a single unit, or can be spread across a number of components in any number of ways. When performed by software, the methods may be executed by a processor, such as a general purpose computer, based on instructions stored on a computer-readable medium. If desired, the instructions can be stored on the medium in a compressed and/or encrypted format.

Moreover, other implementations of the present application will be apparent to those skilled in the art from consideration of the specification and practice of the teachings of the present application. Various aspects and/or components of the described example implementations may be used singly or in any combination. It is intended that the specification and example implementations be considered as examples only, with the true scope and spirit of the present application being indicated by the following claims.

What is claimed is:

1. A method, comprising:
conducting data pipelining for generating machine learning models for predicting treatment transition outcomes, comprising:
generating a treatment pathway graph;
extracting one or more sets of valid treatment options from the treatment pathway graph;
extracting valid predictors from the treatment pathway graph; and for provision of subject patient data in the machine learning models for predicting treatment transition outcomes:
extracting a current treatment pattern from the subject patient data;
determining a patient node on the treatment pathway graph;
for a selection of a valid treatment option set from the sets valid treatment options on the treatment pathway graph:
extracting selected valid treatment option set from the sets of valid treatment options from the treatment pathway graph;
determining associated ones of the one or more sets of valid treatment options based on the extracted selected valid treatment option set from the sets of valid treatment options;
determining ones of the machine learning models for predicting treatment transition outcomes associated with the selected valid treatment option set from the sets of valid treatment options;
executing on the ones of the machine learning models, each of the associated ones of the one or more sets of valid treatment options to predict treatment transition outcomes for all of the associated ones of the one or more sets of valid treatment options; and
providing the predicted treatment transition outcomes.

2. The method of claim 1, wherein the generating the treatment pathway graph comprises:
extracting a treatment timeline from electronic health records;
correcting gaps in the treatment timeline;
detecting treatment transitions from the corrected treatment timeline; and
generating the treatment pathway graph from the treatment transitions.

3. The method of claim 1, wherein the extracting valid predictors from the treatment pathway graph comprises:
dividing training data from electronic health records into each treatment path in the treatment pathway graph;
extracting first valid predictors for each treatment path; and
for each node in the treatment graph, extracting second valid predictors from all combinations of treatment paths starting from each node in the treatment pathway graph; and
extracting from the treatment pathway graph a set of universal valid predictors applicable to all valid treatment options of the treatment pathway graph.

4. The method of claim 3, further comprising generating the machine learning models for predicting treatment transition outcomes, the generating comprising:
dividing training data from electronic health records into each treatment path in the treatment pathway graph;
constructing first machine learning models for predicting treatment transition outcomes for each treatment path from the first valid predictors; and
constructing second machine learning models for predicting treatment transition outcomes for each treatment path from the second valid predictors; and
constructing third machine learning models for predicting treatment transition outcomes for each treatment path from the universal valid predictors.

5. The method of claim 1, further comprising:
determining associated ones of the one or more sets of valid treatment options based on the patient node; and
determining ones of the machine learning models for predicting treatment transition outcomes associated with the patient node.

6. A non-transitory computer readable medium, storing instructions for executing a process, the instructions comprising:
conducting data pipelining for generating machine learning models for predicting treatment transition outcomes, comprising:
generating a treatment pathway graph;
extracting one or more sets of valid treatment options from the treatment pathway graph;
extracting valid predictors from the treatment pathway graph; and
for provision of subject patient data in the machine learning models for predicting treatment transition outcomes:
extracting a current treatment pattern from the subject patient data;
determining a patient node on the treatment pathway graph;
for a selection of a valid treatment option set from the sets valid treatment options on the treatment pathway graph:
extracting selected valid treatment option set from the sets of valid treatment options from the treatment pathway graph;
determining associated ones of the one or more sets of valid treatment options based on the extracted selected valid treatment option set from the sets of valid treatment options;
determining ones of the machine learning models for predicting treatment transition outcomes associated with the selected valid treatment option set from the sets of valid treatment options;
executing on the ones of the machine learning models, each of the associated ones of the one or more sets of valid treatment options to predict treatment transition outcomes for all of the associated ones of the one or more sets of valid treatment options; and
providing the predicted treatment transition outcomes.

7. The non-transitory computer readable medium of claim 6, wherein the generating the treatment pathway graph comprises:
extracting a treatment timeline from electronic health records;
correcting gaps in the treatment timeline;
detecting medication transitions from the corrected treatment timeline; and
generating the treatment pathway graph from the treatment transitions.

8. The non-transitory computer readable medium of claim 6, wherein the extracting valid predictors from the treatment pathway graph comprises:
dividing training data from electronic health records into each treatment path in the treatment pathway graph;
extracting first valid predictors from each treatment path; and
for each node in the treatment graph, extracting second valid predictors from all combinations of treatment paths starting from each node in the treatment pathway graph; and extracting from the treatment pathway graph a set of universal valid predictors applicable to all valid treatment options of the treatment pathway graph.

9. The non-transitory computer readable medium of claim 8, the instructions further comprising generating the machine learning models for predicting treatment transition outcomes, the generating comprising:
dividing training data from electronic health records into each treatment path in the treatment pathway graph;
constructing first machine learning models for predicting treatment transition outcomes for each treatment path from the first valid predictors; and
constructing second machine learning models for predicting treatment transition outcomes for each treatment path from the second valid predictors; and
constructing third machine learning models for predicting treatment transition outcomes for each treatment path from the universal valid predictors.

10. The non-transitory computer readable medium of claim 6, the instructions further comprising:
determining associated ones of the one or more sets of valid treatment options based on the patient node; and
determining ones of the machine learning models for predicting treatment transition outcomes associated with the patient node.

11. An apparatus, comprising:
a processor, configured to conduct data pipelining for generating machine learning models for predicting treatment transition outcomes, by:
generating a treatment pathway graph;
extracting one or more sets of valid treatment options from the treatment pathway graph;
extracting valid predictors from the treatment pathway graph; and
for provision of subject patient data in the machine learning models for predicting treatment transition outcomes:
extract a current treatment pattern from the subject patient data;
determine a patient node on the treatment pathway graph;
for a selection of a valid treatment option set from the sets of valid treatment options on the treatment pathway graph:
extract selected valid treatment option set from the sets of valid treatment options from the treatment pathway graph;
determine associated ones of the one or more sets of valid treatment options based on the extracted selected valid treatment option set from the sets of valid treatment options;
determine ones of the machine learning models for predicting treatment transition outcomes associated with the selected valid treatment option set from the sets of valid treatment options;
execute on the ones of the machine learning models, each of the associated ones of the one or more sets of valid treatment options to predict treatment transition outcomes for all of the associated ones of the one or more sets of valid treatment options; and
provide the predicted treatment transition outcomes.

12. The apparatus of claim 11, wherein the processor is configured to generate the treatment pathway graph by:
extracting a treatment timeline from electronic health records;
correcting gaps in the treatment timeline;
detecting treatment transitions from the corrected treatment timeline; and
generating the treatment pathway graph from the treatment transitions.

13. The apparatus of claim 11, wherein the processor is configured to extract valid predictors from the treatment pathway graph by:
dividing training data from electronic health records into each treatment path in the treatment pathway graph;
extracting first valid predictors from each treatment path; and
for each node in the treatment graph, extracting second valid predictors from all combinations of treatment paths starting from each node in the treatment pathway graph; and
extracting from the treatment pathway graph a set of universal valid predictors applicable to all valid treatment options of the treatment pathway graph.

14. The apparatus of claim 13, the processor further configured to generate the machine learning models for predicting treatment transition outcomes, by:
dividing training data from electronic health records into each treatment path in the treatment pathway graph;
constructing first machine learning models for predicting treatment transition outcomes for each treatment path from the first valid predictors; and
constructing second machine learning models for predicting treatment transition outcomes for each treatment path from the second valid predictors; and
constructing third machine learning models for predicting treatment transition outcomes for each treatment path from the universal valid predictors.

15. The apparatus of claim 11, the processor further configured to:
determine associated ones of the one or more sets of valid treatment options based on the patient node; and
determine ones of the machine learning models for predicting treatment transition outcomes associated with the patient node.

* * * * *